United States Patent [19]

Stainmesse et al.

[11] Patent Number: 5,174,930
[45] Date of Patent: Dec. 29, 1992

[54] PROCESS FOR THE PREPARATION OF DISPERSIBLE COLLOIDAL SYSTEMS OF AMPHIPHILIC LIPIDS IN THE FORM OF OLIGOLAMELLAR LIPOSOMES OF SUBMICRON DIMENSIONS

[75] Inventors: Serge Stainmesse, Choisy le Roi; Hatem Fessi, Paris; Jean-Philippe Devissaguet, Neuilly sur Seine; Francis Puisieux, Maisons-Alfort, all of France

[73] Assignee: Centre National de la Recherche Scientifique (CNRS), Paris, France

[21] Appl. No.: 666,469

[22] Filed: Mar. 6, 1991

Related U.S. Application Data

[63] Continuation of Ser. No. 371,585, Jun. 26, 1989, abandoned, which is a continuation-in-part of Ser. No. 140,246, Dec. 31, 1987, Pat. No. 5,049,322.

[30] Foreign Application Priority Data

Dec. 31, 1986 [FR] France ............................ 86 18444
Jun. 30, 1988 [FR] France ............................ 88 08874

[51] Int. Cl.⁵ ........................ A61K 9/127; B01J 13/12
[52] U.S. Cl. ......................... 264/4.6; 264/4.1; 424/450; 428/402.2
[58] Field of Search .............. 264/4.1, 4.33, 4.6; 427/213.36; 424/450

[56] References Cited

U.S. PATENT DOCUMENTS

| | | | |
|---|---|---|---|
| 3,242,051 | 3/1966 | Hiestand et al. | 264/4.3 X |
| 3,664,963 | 5/1972 | Pasin | 427/213.36 |
| 3,780,195 | 12/1973 | Balassa | 264/4.6 X |
| 4,021,364 | 5/1977 | Speiser et al. | 427/213.34 X |
| 4,107,288 | 8/1978 | Oppenheim et al. | 264/4.3 X |
| 4,235,871 | 11/1980 | Papahadjopoulos et al. | 424/450 X |
| 4,588,578 | 5/1986 | Fountain et al. | 428/402.2 |
| 4,610,868 | 9/1986 | Fountain et al. | 264/4.1 X |
| 4,637,905 | 1/1987 | Gardner | 264/4.1 |
| 4,687,661 | 8/1987 | Kikuchi | 424/38 |
| 4,726,966 | 2/1988 | Kawashima et al. | 427/213.36 |
| 4,761,288 | 8/1988 | Mezei | 424/450 |
| 4,830,858 | 5/1989 | Payne et al. | 424/450 |
| 4,844,904 | 7/1989 | Hamaguchi et al. | 264/4.3 X |

FOREIGN PATENT DOCUMENTS 158441 10/1985 European Pat. Off. ............ 424/450

OTHER PUBLICATIONS

Batzri, S. et al., 'Single Bilayer Liposomes Prepared Without Sonication', *Biochim. Biophys. Acta*, vol. 298, (1973), pp. 1015–1019.

Szoka, Jr., F. et al., 'Procedure for Preparation of Liposomes...', *PNAS*, vol. 75, No. 9, (1978), pp. 4194–4198.

Kim, S. et al., 'Preparation of Cell-Size Unilamellar Liposomes...', *Biochim. Biophys. Acta*, vol. 646, (1981), pp. 1–9.

Kim, S. et al., 'Preparation of Multivesicular Liposomes', *Biochim. Biophys. Acta*, vol. 728, (1983), pp. 339–348.

*Primary Examiner*—Robert L. Stoll
*Assistant Examiner*—John M. Covert
*Attorney, Agent, or Firm*—Young & Thompson

[57] ABSTRACT

Dispersible colloidal systems of amphiphilic lipids in the form of oligolamellar liposomes of submicron dimensions are prepared by combining a first liquid phase consisting essentially of a solution of the lipids with a greater amount of a second liquid phase consisting essentially of water. The solvent for the first liquid phase is miscible in all proportions with water. If desired, the first liquid phase may also contain a substance A in solution therewith, such as cholesterol. An additional substance B, which is a biologically active substance, may be present in the first phase if it is lipophilic, and in the second phase if it is hydrophilic.

13 Claims, No Drawings

PROCESS FOR THE PREPARATION OF DISPERSIBLE COLLOIDAL SYSTEMS OF AMPHIPHILIC LIPIDS IN THE FORM OF OLIGOLAMELLAR LIPOSOMES OF SUBMICRON DIMENSIONS

This application is a continuation of application Ser. No. 07/371,585, filed Jun. 26, 1989, now abandoned, which is a CIP of U.S. Ser. No. 140,246, filed Dec. 31, 1987, now U.S. Pat. No. 5,049,322.

The subject of the present invention is a novel procedure for the preparation of dispersible colloidal systems of a substance in the form of spherical particles of the vesicular type and of a size less than 500 nm (nanocapsules).

Nano-vesicular systems, including nanocapsules varying in size from 50 to 500 nm and consisting of a solid or liquid central core enveloped by a continuous, water-insoluble membrane, have already been described in the literature. The constituents of the membrane may be synthetic (polymers) or naturally-occurring (proteins) macromolecules, or lipids (liposomes).

Sub-microscopic polymeric particles possessing a diameter less than 500 nm are known, in particular from the patents BE-A-803 034, BE-A-839 748, BE-A-869 107, FR-A-2 504 408 and FR-A-2 515 960. According to BE-A-808 034 and -839 748, the sub-microscopic particles are formed by micellar polymerization of a monomer such as a derivative of acrylic acid. Similarly, BE-A-869 107, FR-A-2 504 408 and FR-A-2 515 960 describe the preparation of nanoparticles and of biodegradable nanocapsules obtained by the polymerization of an alkyl cyanoacrylate and containing a biologically active substance. The methods resort to polymerization in solution and are thus limited to using a limited number of polymers which can be prepared, in particular, by vinyl addition and are not suitable for naturally occurring or semi-synthetic polymers. Furthermore, it is difficult to control the molecular weight of the polymer constituting the nanoparticles and it is necessary, particularly when their biological use is under consideration, to remove the residual monomers and oligomers and, where necessary, the excess reagents involved in the polymerization reaction (initiator and catalyst), as well as surfactants if they are used at high concentration or are not biocompatible. In actual fact, the purification often proves to be onerous (ultracentrifugation, dialysis) since the filtration of the nanoparticles and nanocapsules is not always possible on account of their size.

The preparation of protein nanocapsules, in particular those made of gelatin, has also been described. Thus, Krause et al. (Pharm. Research, 239 (1985)) prepared nanocapsules of gelatin, the content of which was lipophilic (chloroform), starting from an emulsion of chloroform in a continuous aqueous phase (albumin solution). This emulsion is then desolvated by means of sodium sulfate. The nanocapsules are then hardened by means of glutaraldehyde, the excess of which must be destroyed by the use of sodium metabisulfite which, in turn, must be removed. Furthermore, the stability of the chloroform in the nanocapsule seems to be limited by its tendency to evaporate: the solvent may escape from the nanocapsules which, however, retain the lipophilic substance initially dissolved in the chloroform solution.

Unilamellar liposomes may be considered to be nanovesicles. The preparation is carried out by vigorous sonication of an aqueous disperson of phospholipids which leads to a particle size varying between 20 and 100 nm, but which entails the disadvantage of the risk of oxidation and other types of modification associated with sonication. Batzri et al. (Biochim. Biophys, Acta, 298, 1015 (1973)) suggested a method not involving sonication which is carried out by injecting (Hamilton syringe) a solution of egg white lecithin into a aqueous phase and which leads to the formation of unilamellar liposomes of about 25 nm. Nonetheless, this is a laboratory procedure which cannot be extended to other types of substances.

All of the methods described above are only applicable to certain classes of molecules and necessarily involve operations which are expensive (ultracentrifugation, sonication, etc) or hard to control (polymerization) without ensuring that the size of the particles is acceptably homogeneous or even that the particles are sufficiently small (less than 500 nm) such as would assure their long-term stability in the form of a colloidal suspension.

The invention proposes a new process for the preparation of nanocapsules which is free from the above-mentioned disadvantages and which can be used both for naturally occurring and synthetic polymeric substances and for various organic substances (medicines, lipids, etc) or minerals (salts, pigments, etc) as well as for mixtures of them.

The subject of the invention is a process for the preparation of dispersible colloidal systems in the form of spherical particles of the vesicular type possessing a size less than 500 nm (nanocapsules), the wall of which is constituted by a substance A and the core by a substance B, comprising:

(1) the preparation of a liquid phase consisting essentially of a solution of the substance A in a solvent or in a mixture of solvents containing substance B in solution or as a dispersion, (2) the preparation of a second liquid phase consisting essentially of a non-solvent or a mixture of non-solvents for the substances A and B, and to which one or more surfactants are added, the solvent or the mixture of solvents of the first phase being miscible in all proportions with the non-solvents or mixture of non-solvents of the second phase, (3) the addition of the first phase to the second phase with moderate stirring so as to produce a colloidal suspension of nanocapsules, (4) if desired, the removal of all or part of the solvent or mixture of solvents or of the non-solvent or mixture of non-solvents so as to give rise to a colloidal suspension containing the desired concentration of nanocapsules or, to lead to a powder of nanocapsules.

In step (3), the nanocapsules are formed practically instantaneously. The solution becomes milky white and shows the Tyndall effect characteristic of colloidal suspensions. At this stage, it is preferable to add the liquid phase prepared in step (1) to the liquid phase prepared in step (2), particularly if the latter is aqueous. By "moderate stirring" a stirring up to 500 rpm, e.g. about 100 rpm, is meant, such as magnetic stirring.

The "substance A" used according to the process of the invention may be practically any substance sufficiently soluble in a given solvent.

However, in view of the intended applications of the nanocapsules, the "substance A" is preferably a polymer, either a synthetic polymer, for example poly (d,l) lactic acid (PLA) etc, a semi-synthetic polymer such, as for example, cellulose butyrate acetate, ethylcellulose, the phthalate of hydroxymethyl-propylcellulose (HPMCP), etc or a naturally occurring polymer, for example gelatin, gum arabic, etc. Numerous other polymers can be used, for example: the aceto-phthalate of polyvinvyl, the aceto-phthalate of cellulose; maleic acid derivatives (for example "GANTREZ"); the copolymers of acrylic acid and acrylates and acrylic acid polymers (for example EUDRAGIT ®); d or l and (d,l) polylactic acid: the copolymers of lactic acid and glycolic acid, polypeptides, glycol derivatives (derivatives of propiolactone, butyrolactone, pivalolactone, ε-caprolactone, etc); the polymers obtained from cyclic esters of hydroxybutyric acid, hydroxyisobutyric acid, hydroxymethylvaleric acid, phenyl-lactic acid, and hydroxyethylbutyric acid; poly beta benzyl malate: the copolymers of malic acid and benzyl malate; a polyvinylpyrrolidone-vinyl acetate cross-linked copolymer, the alkyl polycyanoacrylates; poly (ethylene-vinyl acetate); water-soluble polymers (gelatin, gum arabic, methylcellulose, etc); oligomers (styrene allyl alcohol), etc.

The "substance B" that it is desired to encapsulate in the substance A can be practically any substance soluble or dispersible in a given solvent.

The "substance B" may be a vegetable or a mineral oil, or any oily substance, for example olive oil, benzyl benzoate, isopropyl myristate, glycerides of fatty acids (for example a MIGLYOL ®), volatile oils, etc . . .

The "substance B" may also be a biologically active substance, in particular an active medicinal ingredient or a precursor of an active medicinal ingredient or even a contrasting agent or a biological reagent.

The "substance B" may also be a pigment, an ink, a lubricant, an agent for treating surfaces, etc.

It is obvious that the process according to the invention can be applied equally to one substance B or several, for example an oil and a biologically active substance dissolved in this latter.

The "solvent" or the mixture of solvents used is a liquid capable of dissolving substance A and possibly substance B (for example, the polymer and possibly the biologically active substance). Moreover, the solvent must be miscible with the non-solvent for the substance used in the preparation. Thus, in most cases, the solvent will be an organic solvent such that the liquid phase (1) will constitute the organic phase whereas the liquid phase (2) will constitute the aqueous phase, but it is possible to use either two organic phases or two aqueous phases provided the conditions regarding solubility, insolubility and miscibility are met. On the other hand, the solvent must be sufficiently volatile for it to be removed if necessary. For example, in the case in which the substance is a polymer, the solvent may be chosen from among a lower alcohol (methanol, ethanol, isopropanol, etc), a lower ketone (acetone, methyl-ethylketone, etc), a light hydrocarbon or a mixture of ligh hydrocarbons (hexane, petroleum ether, etc), a chlorinated lighthydrocarbon (chloroform, methylene chloride, trichloroethylene, etc), or other common light solvents such as acetonitrile, dioxane, etc.

The "non-solvent" or the mixture of non-solvents for substances A and B is a liquid which does not dissolve these substances while being miscible with the solvent used. Thus, for example, when substance A is a polymer such as P.L.A., the solvent may be acetone and the non-solvent may be ethanol or distilled water; if the substance A is for example an acrylic polymer such as EUDRAGIT L100 ®, the solvent may be an alkaline aqueous phase and the non-solvent may be an acidic aqueous phase.

The surfactant(s) (or emulsifying agents) added to the liquid phase (2) may be naturally occurring (lecithins), or synthetic, anionic (for example sodium laurylsulfate), cationic (for example quaternary ammonium) or non-ionic (for example, monoesters of sorbitan which may or may not contain a polyoxyethylene residue, ethers formed between fatty alcohols and polyoxyethylene glycols, polyoxyethylene-polypropylene glycol, etc). However, it is possible to add one or more surfactants of the same type as those mentioned above to the liquid phase (1) in order to improve the stability of the suspension in particular.

In step (4) the solvents and non-solvents may be completely removed, for example by lyophilization. In this way it is possible to obtain lyophilized nanocapsules which can be stored for long periods.

The proportion of surfactants in the colloidal suspension prepared in step (3) to which they have been added may vary in particular from 0.1% to 10% by weight, and lies preferably between 0.2 and 2% by weight.

In the case in which substance A is a polymer, the concentration of the polymer in the solvent or the mixture of solvents may vary between 0.1 and 10%, and lies preferably between 0.2 and 2% by weight.

The ratio of the volumes of solvents and non-solvents must be such as to allow the precipitation of the polymer. As this ratio increases, the size of the nanocapsules diminishes.

The moderate agitation of the preparation in step (3) is dependent on the amount of the substances utilized. It is not necessary for small quantities.

The effect of temperature and pH on the process according to the invention are limited so that it is usually not necessary to work under special conditions. However, when the two phases (1) and (2) used are aqueous, their respective pHs must be different in order for them to comply with the conditions of being a solvent and a non-solvent.

Moreover, the presence of an electrolyte (for example sodium chloride) does not appear to affect the production of nanocapsules. Thus, after the formation of the nanocapsules in step (3) a concentration of 25 mg/ml of sodium chloride does not lead to coalescence or precipitation of the nanocapsules formed.

The nanocapsules prepared according to the invention can be autoclaved if the physical properties of the substance permit this.

The process for the preparation of nanocapsules according to the invention offers the following advantages compared with known processes:

the production of nanocapsules smaller than 500 nm and in particular varying from about 150 to 450 nm by means of a simple method not requiring a supply of energy;

in the case in which the substance A forming the wall is a polymer, the nanocapsules are no longer obtained by polymerization of a monomer but by "nanoprecipitation" of a well-defined polymer;

the utilization of naturally occurring polymers as well as synthetic polymers which are known to be innocuous and which have been used for medical purposes for a very long time;

the utilization of polymers which are of the type which are biocompatible;

the possibility of using polymers which can dissolve in the organism once a particular pH value is attained, thus ensuring that polymer particles do not accumulate in the organism;

the possibility of using polymers which by their nature are bioresorbable, the products of their degradation being completely innocuous;

the production of spherical capsules exhibiting only a slight variation in size and a content/container ratio which is very high (for example the ratio active ingredient/polymer).

The following examples illustrate the invention. The nanocapsules obtained are visible in the transmission electron microscope (×25000–150000) and, after negative staining with phosphotungstic acid, appear as approximately round, non-contrasted particles.

EXAMPLE 1

Preparation of nanocapsules of a polymer containing an organic liquid

On the one hand, 125 mg of the copolymer of vinyl chloride and vinyl acetate (Rhodopas ® AX 85-15) and 0.5 ml of benzyl benzoate are dissolved in 25 ml of acetone.

On the other hand, 125 mg of the mixed polymer formed between ethylene oxide and propylene glycol (PLURONIC F68 ® or POLOXAMER 188 ®), a non-ionic surfactant, are dissolved in 50 ml of purified water.

The acetone phase is poured into the aqueous phase with moderate magnetic stirring (about 100 r.p.m.). The aqueous phase immediately turns milky-white with bluish opalescence as a result of the formation of the nanocapsules, the wall of which is constituted by the vinyl copolymer and the core by benzyl benzoate.

The acetone is removed under reduced pressure (water pump vacuum) and the suspension is concentrated to the desired volume, for example 10 ml, by removal of water under the same conditions.

The concentrated suspension is filtered through a glass frit (pores of 9–15 μm) and the diameter of the nanocapsules measured in a diffractometer equipped with a laser beam (NANOSIZER ® supplied by the Coultronics Company) is about 410 nm with a dispersion index of 2.

EXAMPLE 2

Preparation of nanocapsules of polymers containing indomethacin (lipophilic active ingredient)

a) On the one hand, 125 mg of polyisobutylcyanoacrylate, 0.5 ml of benzyl benzoate and 15 mg of indomethacin are dissolved in 25 ml of acetone.

On the other hand, 125 mg of the mixed polymer formed between ethylene oxide and propylene glycol (PLURONIC F68 ®) are dissolved in 50 ml of purified water.

The process then adopted is the same as that indicated in Example 1 and a suspension of nanocapsules is obtained, the diameter of which is about 240 nm with a dispersion index of 2. After ultracentrifugation, titration of indomethacin in the aqueous phase used as dispersion medium shows that the nanocapsules contain 98% of the active ingredient.

b) Pharmacological assay:

When administered by the oral route to the fasted rat (5 mg/kg of indomethacin) the suspension of nanocapsules leads to a more rapid and more complete digestive absorption of the indomethacin than that observed after administration of the same dose of indomethacin in solution. After repeated administration to the fasted rat (5 mg/kg of indomethacin on 3 successive days) the suspension of nanocapsules results in improved digestive tolerance, as evidenced by the number of ulcerations and hemorrhages, compared with that observed after administration of the same dose of indomethacin in solution.

When administered by the intravenous route to the rat (5 mg/kg of indomethacin) the suspension of nanocapsules gives rise to a chronological profile of plasma concentrations of indomethacin which demonstrates an increased extravascular distribution of the active ingredient compared with that found after injection of indomethacin in solution (increase of the volume of distribution of indomethacin by a factor of approximately 2) followed by slower elimination (increase of the biological half-life of indomethacin by a factor of approximately 2).

EXAMPLE 3

Preparation of "empty" nanocapsules

The process described in Example 1 is employed but benzyl benzoate is replaced by ethyl ether (0.5 ml). After formation of the nanocapsules, the acetone and ether are carefully removed under reduced pressure (water pump) and the suspension of nanocapsules is concentrated to the desired volume, for example 10 ml, by removal of water.

The diameter of the nanocapsules is about 228 nm with a dispersion index of 1.5.

EXAMPLE 4

Preparation of nanocapsules of a polymer containing a lipophilic dye

The same process as that indicated in Example 3 is employed but 5 mg of Sudan III, a lipophilic dye, is added to the acetone phase.

After removal of the acetone and ether and concentration of the aqueous phase acting as dispersion medium to 10 ml, the diameter of the nanocapsules is about 175 nm with a dispersion index of 1.

The suspension of nanocapsules is then placed in contact with 5 ml of ethyl ether and the mixture is agitated by repeated inversion for a period of 5 mn. The ethereal phase remains colourless, thus demonstrating that the lipophilic dye has been completely encapsulated.

EXAMPLE 5

Preparation of nanocapsules of a polymer containing a hydrophilic dye

On the one hand, 125 mg of poly (d,l) lactic acid, 3.5 mg of ethythrosine, a hydrophilic dye, and 0.4 ml of propylene glycol are dissolved in 25 ml of an acetone/tetrahydrofuran (50/50, v/v) mixture.

On the other hand, 0.8 ml of the mono-oleate of sorbitan (Span 80 ®), a non-ionic surfactant, is dissolved in 50 ml of a heptane/silicone oil/acetone (80/10/10, v/v) mixture.

The acetone/tetrahydrofuran phase is added to the heptane/silicone/acetone phase with magnetic stirring. After concentration to a volume of 10 ml under reduced pressure, the diameter of the nanocapsules is about 490 nm with a dispersion index of 0.5.

The suspension of nanocapsules is agitated in the presence of 5 ml of purified water under the same conditions as those described in Example 4. The aqueous phase remains colourless, thus demonstrating that the hydrophilic dye has been completely encapsulated by the polymer.

EXAMPLE 6

Preparation of nanocapsules containing a lipid

The process employed is the same as that described in Example 1 but benzyl benzoate is replaced by a vegetable oil (peanut oil, for example). After filtration through a glass frit, trehalose (200 mg/ml) is added to the suspension to facilitate lyophilization, and the mixture is lyophilized. After resuspension of the powder of nanocapsules in 10 ml of purified water, their diameter is about 490 nm with a dispersion index of 2. Even after prolonged standing no phase separation is observed, thus demonstrating that the oil is still encapsulated in the polymer after lyophilization.

EXAMPLE 7

Preparation of nanocapsules of a polymer containing a mineral solid

On the one hand, 125 mg of an acrylic polymer (EUDRAGIT L100, obtained from the Röhm-Pharma Company) are dissolved in 50 ml of purified water to which 2 ml of 0.1N sodium hydroxide solution is added.

On the other hand, 125 mg of a mixed polymer formed between ethylene oxide and propylene glycol (PLURONIC F68 ®) are dissolved in 100 ml of purified water to which 0.45 ml of glacial acetic acid are added and 100 mg of particulate silicon carbide (mean diameter 450 nm, dispersion index 1) are dispersed in this phase.

The alkaline phase containing the polymer is added to the silicon carbide dispersed in the acidic phase with moderate magnetic stirring (about 100 r.p.m.). The acrylic polymer encapsulates the solid particles of silicon carbide and the nanocapsules thus obtained have a mean diameter of 475 nm with a dispersion index of 1.

It is possible that the nanocapsules produced according to the invention will find uses in many areas of technology, particularly those requiring microcapsules but considerably reduced in size ($\times 10^{-3}$), rendering their suspensions more stable and easier to use.

As "vectors" of medicines in human and animal therapy, the nanocapsules offer the prospects of:
  attaining new sites of action, in particular intracellular sites, and even intralysosomal sites;
  using new routes of administration for known medicines by increasing the stability and/or the absorption of the medicines, or by making available insoluble medicines in forms which can be injected by the intravascular route;
  modifying the tissue distribution of the medicines by better targeting towards favourable sites of action and/or by diverting them from sites at which they produce undesirable, or even toxic, effects (improvement of the therapeutic index).

In pharmacy, the colloidal dispersions in the form of nanocapsules make it possible to:
  prepare injectable forms of insoluble medicines,
  stabilize a medicamentous active ingredient, and
  prepare coatings of galenical forms starting from aqueous dispersions of film-forming polymers.

In the field of agrochemistry, the nanocapsule can be used as vehicles for insecticides, pesticides etc . . . Their size leads to the expectation of a more powerful action as a result of better penetration through the cuticle. The low viscosity of the dispersion enables atomization to be carried out very easily in the form of droplets of very small size which are more efficacious because they provide more intimate covering.

In the area of paints, varnishes and treatment of surfaces in general, the nanocapsules may function as vehicles of pigments, reagents, strippers, etc . . . in the form of aqueous dispersions of very low viscosity, easy to atomize or apply and which can, if necessary, be made viscous and even adhesive (resuspension of the nanocapsules in an appropriate vehicle). The small size of the nanocapsules leads to a very fine deposition and to a very high homogeneity, for example, of pigmentation.

The nanocapsules prepared according to the invention can also be used in the fields of printing and reproduction graphics, the treatment of surfaces of textiles and fibres, photography, lubrication, etc . . . A further object of the present invention is a process for the preparation of dispersible colloidal systems of amphiphilic lipids in the form of oligolamellar liposomes of submicron dimensions.

Numerous reports are known which describe the preparation and utilization of liposomes, in particular as vehicles of biologically active substances such as medicines, proteins, enzymes, diagnostic reagents or cosmetic products. Thus, water-soluble substances can be encapsulated in the aqueous spaces of the liposome, or lipophilic substances can be incorporated into the lipid wall.

A process for the preparation of oligolamellar vesicular systems has already been described by Bangham and al. (J. Mol. Biol. 13, 238-252; 1965). According to this procedure, the lipids and the lipophilic substances are dissolved in an organic solvent and treated with an aqueous phase with vigorous shaking. However, this process, like most of the known processes which are derived from it, does not make it possible to obtain directly liposomes of particle size less than a micrometer, a size which would lead to a much greater stability of the particles and their dispersions.

The invention provides a simple process for the preparation of liposomes of submicroscopic dimensions which is applicable on a large scale.

The invention does relate to a process for the preparation of dispersible colloidal systems of amphiphilic lipids in a form of oligolamellar liposomes of submicron dimensions, the wall of which is constituted by the said lipids and optionally by a substance A and the interior of which is constituted by water or an aqueous solution, and may contain a substance B, comprising:
  (1) the preparation of a liquid phase consisting essentially of a solution of amphiphilic lipids and optionally of the substance A in a solvent or in a mixture of solvents, and which may contain the substance B in solution,
  (2) the preparation of a second liquid phase consisting essentially of water or an aqueous solution of the substance B,
  (3) the addition, with moderate stirring, of the first phase to the second phase so as to form a colloidal suspension of liposomes,
  (4) if desired, the removal of all or part of the solvent or the mixture of solvents and of water so as to form a colloidal suspension of liposomes of the desired concentration.

The substance A, of lipophilic nature, is intended to modify the physical (electric charge, rigidity) or chemical properties of the wall. It may be cholesterol, stearylamine, phosphatidic acid, alpha-tocopherol, a nonionic surfactant, etc . . .

The substance B is a biologically active substance, in particular a medicamentous active principle or a medicamentous precursor, a biological reagent or a cosmetic product. Substance B is introduced into phase (1) if it is lipophilic and into phase (2) if it is hydrophilic.

The amphiphilic lipids may be glycolipids, phosphoaminolipids, and in particular the phospholipids, for example the lecithins (of egg white, soya, etc . . . ).

The solvent is preferably an alcohol miscible with water in all proportions, in particular ethanol.

The concentration of the lipids in the solvent may be from 0.1 to 10% by weight, preferably from 1 to 5% by weight.

It is advantageous that the volume of the solvent used for phase (1) be comprised between 5 and 100%, for example about 50%, of the volume of water of phase (2), in order for liposomes of small size (in particular from 100 to 300 nm) to be formed.

Thus, the invention makes it possible to obtain medicines, in particular in an injectable form, and cosmetic products which are very stable.

The following examples illustrate the invention.

| Example 1: Preparation of liposomes. | |
|---|---|
| Organic phase 1 | |
| soya lecithin (Epikuron 170) | 2.0 g |
| absolute ethanol | 50.0 g |
| aqueous phase 2 | 100.0 g |
| water | |

Phase 1 is added to phase 2 with magnetic stirring. The mixture immediately becomes opalescent as a result of the formation of liposomes. The mean size of the liposomes, measured immediately after preparation, in a laser beam diffractometer (NANOSIZER® from Coultronics), is 180 nm, with a mean dispersion index of 0.5.

The alcohol is removed under reduced pressure and the liposome suspension is filtered through a glass frit (pores 9-15 nm).

The size of the liposomes, when measured again in the filtrate, remains unchanged.

Examination by means of transmission microscopy shows oligolamellar liposomes of homogeneous size.

EXAMPLE 2

Preparation of liposomes containing cholesterol (variant of example 1)

The procedure is the same as in example 1 except that 0.03 g of cholesterol is added to the alcoholic phase. The liposomes obtained possess the same properties as those in example 1.

EXAMPLE 3

Variant of example 1

The procedure is the same as in example 1 except that soya lecithin is replaced by egg white lecithin. The liposomes obtained possess the same properties as those in example 1.

EXAMPLE 4

Variant of example 2

The procedure is the same as in example 2 except that soya lecithin is replaced by egg white lecithin. The liposomes obtained possess the same properties as those in example 1.

EXAMPLE 5

Preparation of liposomes containing a water-soluble active principle.

The procedure is the same as in example 2 except that 0.20 g of ampicillin (sodium salt) is added to the aqueous phase.

The level of incorporation of ampicillin in the liposomes, measured after separation of the liposomes from the aqueous phase by chromatography on Sephadex gel, is 10%.

EXAMPLE 6

Preparation of liposomes containing a lipophilic active principle

The procedure is the same as in example 1 except that 66.7 mg of muramyl-tripeptide-cholesterol are added to the organic phase. The level of incorporation of the active principle is 100%.

We claim:

1. A process for the preparation of dispersible colloidal systems of amphiphilic lipids in the form of oligolamellar liposomes of submicron dimensions, the wall of which is constituted by said lipids and the interior of which is constituted by water or by an aqueous solution, comprising:
   combining (1) a first liquid phase consisting essentially of a solution of said lipids in a volatile organic solvent for said lipids or in a mixture of volatile organic solvents for said lipids, and (2) a greater amount of a second liquid phase consisting essentially of water, by pouring one of the phases into the other, so as substantially instantaneously to form a colloidal suspension of oligolamellar liposomes having a size ranging from about 100 to about 300 nm and comprising a core of said second phase surrounded by a layer of said lipids, said solvent or mixture of solvents of the first phase being miscible in all proportions with water, said process being performed in the absence of elevated temperature.

2. The process according to claim 1, wherein the amphiphilic lipids are phospholipids.

3. The process according to claim 1, wherein said solvent is an alcohol.

4. The process according to one of the claim 3, wherein the alcohol is ethanol.

5. The process according to claim 1, wherein the concentration of the lipids in the solvent or mixture of solvents is from 0.1 to 10% by weight.

6. The process according to claim 5, wherein the concentration of the lipids in the solvent or mixture of solvents is from 1 to 5% by weight.

7. The process according to claim 1, wherein the volume of solvents of said first phase is comprised between 5 and 100% of the volume of said second phase.

8. The process according to claim 1, wherein said first liquid phase further comprises a lipophilic substance A in solution therewith, said substance A being soluble in said solvent or mixture of solvents.

9. The process according to claim 8, wherein said substance A is selected from the group consisting of cholesterol, stearylamine, phosphatidic acid, alphatocopherol, and non-ionic surfactants.

10. The process according to claim 1, wherein said second phase further comprises a water-soluble biologically active substance B in solution therewith.

11. The process according to claim 10, wherein said substance B is a sodium salt of ampicillin.

12. The process according to claim 1, further comprising removing part of the solvent or mixture of solvents and the water, to form a colloidal suspension of liposomes having a desired concentration.

13. The process according to claim 1, wherein said first liquid phase further comprises a lipophilic biologically active substance in solution therewith.

* * * * *